US006908467B2

(12) United States Patent
Ip et al.

(10) Patent No.: US 6,908,467 B2
(45) Date of Patent: Jun. 21, 2005

(54) SUPREME DISTRACTER

(75) Inventors: Wing Yuk Ip, Laguna (HK); Daniel Cheng Chi Hang, Wan Tsui Estate (HK)

(73) Assignee: The University of Hong Kong, Pokfulam (HK)

(*) Notice: Subject to any disclaimer, the term of this patent is extended or adjusted under 35 U.S.C. 154(b) by 138 days.

(21) Appl. No.: 10/437,767

(22) Filed: May 14, 2003

(65) Prior Publication Data

US 2003/0216739 A1 Nov. 20, 2003

Related U.S. Application Data

(60) Provisional application No. 60/380,383, filed on May 14, 2002.

(51) Int. Cl.[7] .............................................. A61B 17/58
(52) U.S. Cl. ........................................................ 606/72
(58) Field of Search .................. 606/72, 75; 623/21.11, 623/21.15, 21.16, 21.17

(56) References Cited

U.S. PATENT DOCUMENTS

| | | | | |
|---|---|---|---|---|
| 3,466,669 A | * | 9/1969 | Flatt ........................ 623/21.17 |
| 3,939,828 A | * | 2/1976 | Mohr et al. .................... 606/72 |
| 4,414,967 A | * | 11/1983 | Shapiro ........................ 606/75 |
| 4,434,796 A | * | 3/1984 | Karapetian et al. ............ 606/75 |
| 4,444,181 A | * | 4/1984 | Wevers et al. ................. 606/75 |
| 4,838,254 A | * | 6/1989 | Gauthier ....................... 606/75 |
| 4,841,960 A | * | 6/1989 | Garner ......................... 606/75 |
| 4,848,328 A | * | 7/1989 | Laboureau et al. ............ 606/75 |
| 4,899,543 A | * | 2/1990 | Romanelli et al. ............ 60/527 |
| 5,053,038 A | * | 10/1991 | Sheehan ....................... 606/75 |
| 5,474,557 A | * | 12/1995 | Mai ............................. 606/78 |
| 5,660,188 A | * | 8/1997 | Groiso ........................ 128/898 |
| 5,846,247 A | * | 12/1998 | Unsworth et al. ........... 606/108 |
| 6,059,787 A | * | 5/2000 | Allen ........................... 606/75 |
| 6,240,727 B1 | * | 6/2001 | Goldstein et al. ............. 60/528 |
| 6,325,805 B1 | * | 12/2001 | Ogilvie et al. ................ 606/75 |
| 6,485,507 B1 | * | 11/2002 | Walak et al. ............... 623/1.15 |
| 6,509,094 B1 | * | 1/2003 | Shah et al. .................. 428/395 |
| 6,530,564 B1 | * | 3/2003 | Julien ......................... 267/147 |
| 6,550,341 B2 | * | 4/2003 | van Schoor et al. .......... 73/775 |
| 6,685,708 B2 | * | 2/2004 | Monassevitch et al. ....... 606/75 |
| 6,689,136 B2 | * | 2/2004 | Stoffella ...................... 606/72 |

OTHER PUBLICATIONS

"Design and biomechanical study of internal fixation devices for difficult phalangeal fractures" by Wing–yuk IP et al. A thesis submitted for the Degree of Master of Surgery, The University of Hong Kong, Oct. 2002.

* cited by examiner

Primary Examiner—Eduardo C. Robert
Assistant Examiner—Annette Reimers
(74) Attorney, Agent, or Firm—Collard & Roe, P.C.

(57) ABSTRACT

A fixation device for internally or externally fixing fractures comprising at least one nitinol wire having an S-shaped section and two ends wherein each of said two ends forms a hook for hooking into a bone section of a fractured bone. This device can be made from nitinol which has a transformation temperature between 25° C. and 35° C. In addition, this device can have a diameter between 0.6 mm and 5 mm. The device can be inserted using the following process which starts by cooling the wire below a transfer temperature such that the nitinol wire forms in a martensite state. Next, the nitinol wire is inserted into a interphalangeal bone underneath a patients skin. Next, the nitinol wire to heats up inside a patients body above the transfer temperature. Finally, the wire transforms wire from a martensite state to an austenite state wherein when the nitinol wire elongates in a longitudinal direction to generate a distraction force.

4 Claims, 3 Drawing Sheets

SUPREME DISTRACTER

CROSS REFERENCE TO RELATED APPLICATIONS

This Application is Based upon Provisional Application Ser. No. 60/380,383 filed on May 14, 2002 from which priority is claimed under 35 U.S.C. 119(e).

BACKGROUND

The present invention relates generally to a fixation device for fixing fractures. In particular, the present invention relates to an orthopedic fixation device adopted to fix intra-articular hand fractures or fracture subluxation or fracture dislocation in finger joints internally or externally.

In hand surgery, difficult fractures and fracture subluxation or dislocation are frequently treated by open reduction and internal fixation. The proximal interphalangeal joint of fingers is an especially difficult region for treating fractures.

As the fracture is intra-articular, anatomical reduction is crucial to regain joint function and prevent early degenerative changes of the joint. The fracture fixation device must be able to resist the physiological deforming forces namely axial compression, bending and torsion. These physiological deforming forces exert high constant loading to the fracture as the finger flexor muscles and finger extensor muscles have a strong resting muscle tones. These muscles act like rubber bands pulling on the distal end of the digit and constantly acting as a deforming force to displace the fracture.

Moreover, when comminuted fractures occur, articular fragments may collapse and cause joint incongruity. Joint incongruity is undesirable as it will cause early cartilage damage and hence degenerative joint changes.

Juxta-articular fracture is another difficult fracture type. It refers to fracture at the head and the base of the proximal phalanx and middle phalanx.

Head fractures or basal fracture are problematic as the fragments are small and intra-articular. The fragments are linked by the ligaments of the joint. They are difficult to fix by an internal fixation device due to the small size and difficulty in surgical approach. However, to achieve a good functional outcome, the margin of error in reduction is within 1 mm. The flexor and extensor muscles again are a constant deforming force on the internal fixation device to displace the fracture after internal fixation.

Conventionally, inter-phalangeal joint dislocation/subluxation and juxta-articular fractures are treated with open reduction and internal fixation. Fixation devices include small screws or a small metallic pin.

For tiny fracture fragments which cannot be fixed, an external fixator can be used to provide tractional force to the involved joint. The fracture fragments can be reduced by this indirect method which is called ligamentotaxis.

In the worst scenario of comminuted fracture involving the proxmial interphalangeal joint, the joint may need to be fused as fixation is not possible. A fusion will sacrifice all the movement to allow the joint to heal in a useful position, usually at 30–50% flexion.

Other alternatives are artificial proximal interphalangeal joint replacement or joint transfer from another part of the body, usually a toe joint. However, artificial joints are not long lasting and the use of the joint requires the sacrifice of a toe joint.

It is desirable to provide a fixation device to address the above problems. The present invention provides such a fixation device that can reduce these fractures, maintain the fixation by counteracting the physiological deforming force, and hence can replace the conventional treatment methods.

This fixation device can be comprised of a temperature sensitive material such as Nitinol. Nitinol (NiTi) belongs to the family of shape memory alloys, which have been discovered in recent decades. These shape memory alloys have 2 states in solid, one is martensite state and the other is an austenite state. When the material is heated or is above its transformation temperature, it will return to its predetermined shape and it is in an austenite state. In the austenite state, the material is very strong. When the material is cooled, or is below its transformation temperature, it will become soft and pliable. At this temperature, it is in a martensite state and it can easily be manipulated into other shapes.

Another property of shape memory alloys is its supra-elasticity. In the austenite state, the material is very strong, when it is exposed to a critical load, stress will induce martensite transformation. Below this critical loading, the internal stress of Nitinol remains constant despite an increase in strain. By using this property, devices made from Nitinol can generate a constant, continuous force. The force can be compression, distraction, bending or torsion.

The transformation temperature of Nitinol can be determined during the production of the implant. The shapes in the martensite state and in austenite can also be predetermined during the manufacturing procedure. For the purpose of a fixation device in the human body, the transformation temperature can be made at around 25–37° C., preferably 25–35° C. At this temperature, the Nitinol device would be hard and strong. When the device is cooled below the transformation temperature e.g. at 20° C., the device is soft and pliable, i.e. it is in its martensite state. In this soft martensite state, manipulation is easy and placement of a device to a fracture site will be easy and comfortable. There is no need to re-bend the device such as like using a stainless steel implant. The fixation device is expected to be very user-friendly, cooling a Nitinol device to 20° C. is easy as one can just submerge it in cold water. The device can be heated to above the transformation temperature with a simple electrical heating system. When the fixation device is in the body, the body temperature will keep it in the austenite state. The device will continue to be strong and is able to resist high forces.

Because of the supra-elasticity effect of Nitinol, it can generate a constant force when it is in use. When rigid internal fixation is adopted to treat a fracture, fixation in compression is essential to eliminate all the micromotion at a fracture site. Conventional fixation methods include a lag screw or a plate in compression. The compression force is determined at the time of operation. If there is subsequent bone resorption around the screw holes, the compression force will be lost. The target of primary bone healing will not achieved. If the compression force is generated by the supra-elastic property of Nitinol, this compression force is constant as long as the Nitinol device is in situ. What occurs is more resorption around the implant insertion site, the force will still be constant.

A Distraction force is required for treatment of intra-articular fracture, fracture subluxation/dislocation, bone lengthening or soft tissue lengthening. The traditional method of using a distraction device use includes using an external fixator connected to a threaded rod or traction with spring or rubber band. As the tissue lengthens, the tension will decrease. However, the distraction force generated by conventional method is not constant. It is desirable for a distraction device to produce an adequate and constant distraction force. The supra-elastic property of Nitinol can serve this purpose.

SUMMARY

The present invention relates to a fixation device capable of fixing all types of fractures. In particular, the present invention relates to a fixation device to fix juxta-articular fractures occurring in small bones, such as phalangeal bones. It also relates to a fixation device for fracture subluxation and fracture dislocation in an interphalangeal joint of the digits.

The present invention is called a "Supreme Distracter" which is made from nitinol. It comprises two nitinol wires, which are in the shape of an "S" in the top view. Each end of the nitinol wires, is pre-shaped at an acute angle for self-locking anchorage to the bone. In the soft martensite state, the total length of the fixation device is shorter while in the strong austenite state, it lengthens. As the device is inserted to the two sides of the joint at its martensite state, a constant distraction force is produced when the Supreme Distracter changes to its pre-determined shape when heated to an austenite state.

BRIEF DESCRIPTION OF THE DRAWINGS

Other objects and features of the present invention will become apparent from the following detailed description considered in connection with the accompanying drawings which disclose at least one embodiment of the present invention. It should be understood, however, that the drawings are designed for the purpose of illustration only and not as a definition of the limits of the invention.

In the drawings, wherein similar reference characters denote similar elements throughout the several views.

DETAILED DESCRIPTION

Figure 1:
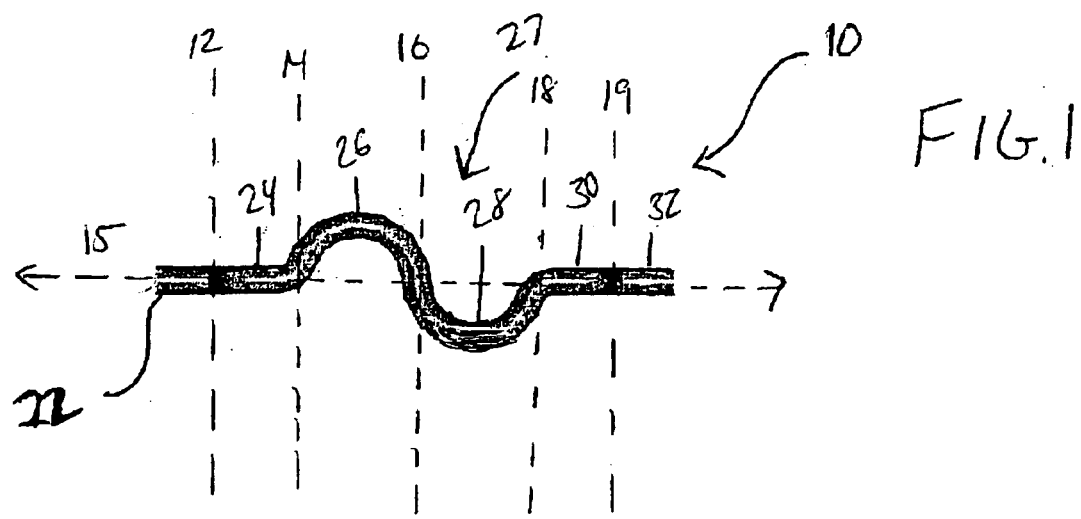
FIG. 1 shows a top view of an example of the device according to the invention.

Referring in detail to the drawings FIG. 1 shows a top view of a distraction device 10 for insertion into a bone of a interphalangeal fracture region. This top view shows that device 10 is divided into different regions via different latitudinal axes 12, 14, 16, 18, and 19. These latitudinal axes divide up device 10 into different regions comprising a first hook 22, an adjacent bent region, a first part of an S curve 26, a second part of an S curve 28, forming a full S-curve 27, an adjacent bent region 30, and a second hook 32. Device 10 extends along a longitudinal axis 15. S curve 27 is used particularly so as to aid in the lengthening of the device 10 so that a larger section of wire is used to create the same overall length but a greater effect of expansion when changing from the martensite state to the austenite state.

For example, the fixation device, is a low profile fixation device, made from Nitinol wire of 1 mm in diameter. Hooks 22 and 32 on its ends as shown in the top view of FIG. 1, are for self-locking anchorage to the bone (See FIG. 4). The original length of the Nitinol wire is 18 mm. In the soft martensite state, the total length of the device is 13 mm while in the strong austenite state; it will lengthen along longitudinal axis 15 into 18 mm. Hence, a distraction force can be produced when the device changes to its original shape when heated.

Figure 2:
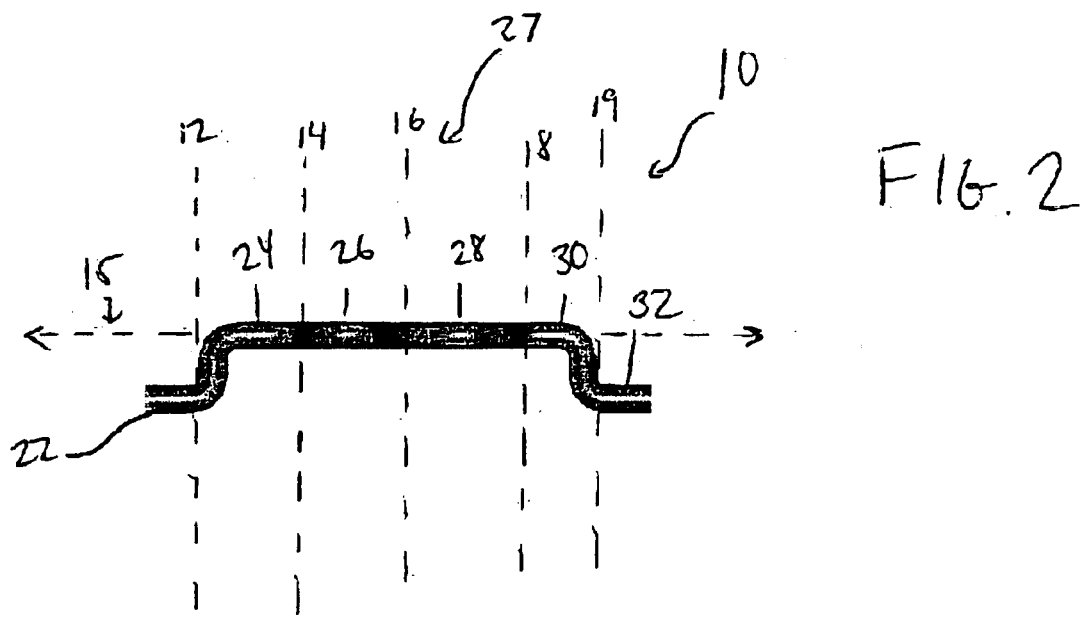
FIG. 2 shows a side view of an example of the device according to the invention.

FIG. 2 shows a side view of device 10 wherein regions 24 and 30 show that device 10 can be bent down such that hooks 22 and 32 are on a different plane than S-curve 27. This bent down region allows the formation of a 90 degree angle to allow hooks 22 and 32 to be inserted into a bone while regions 24 and 30 form stops for the insertion region.

Figure 3:
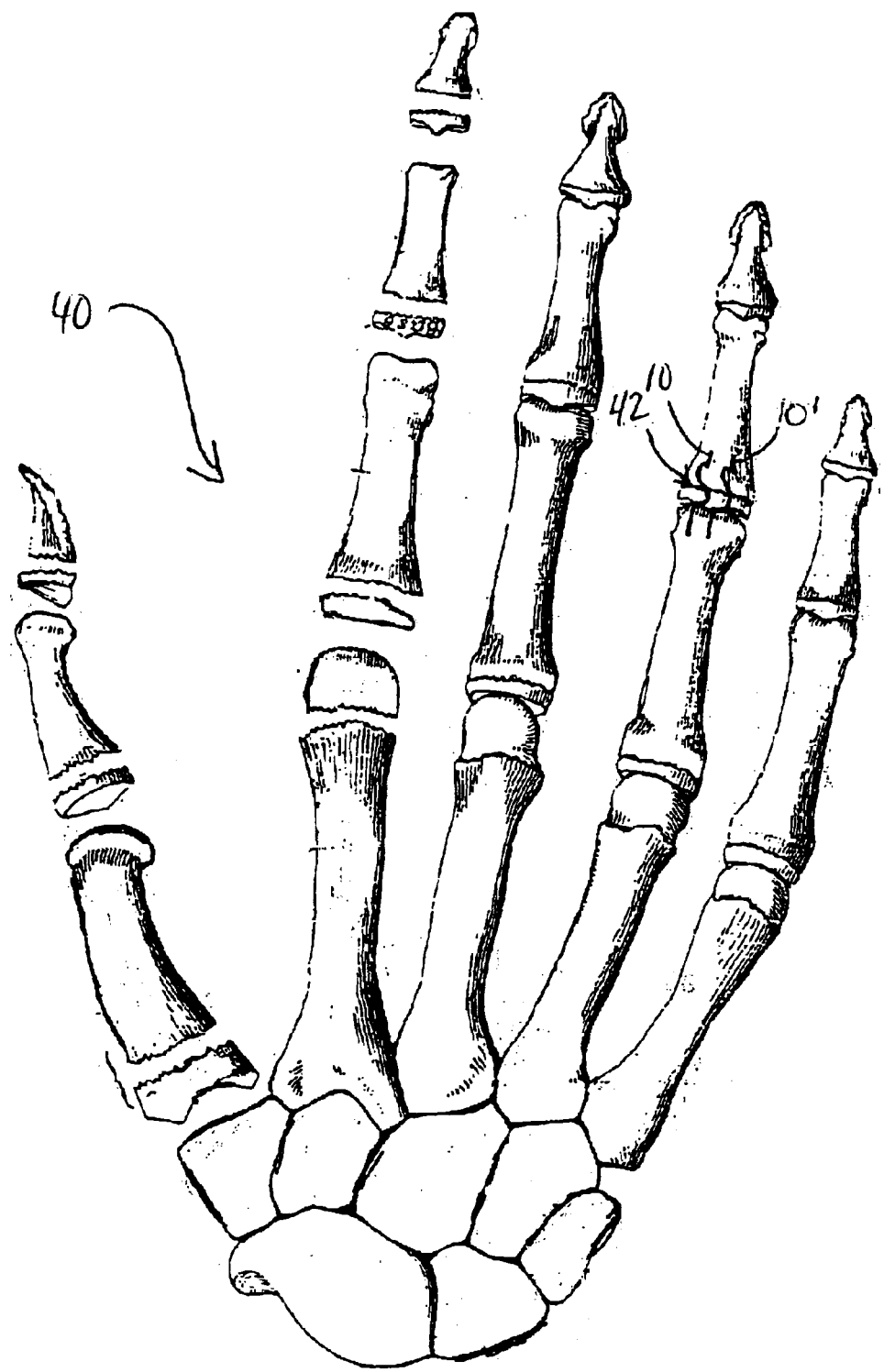
FIG. 3 shows a top view of the device inserted into a proximal interphalangeal joint.

The device fits the bio-mechanical requirements in fractures around finger joint. As shown in FIG. 3 it is inserted into the inter-phalangeal joint 42 in a hand 40 in martensite state at a length of 13 mm. When it is heated up to its transformation temperature, it will tend to lengthen up to a maximal length of 18 mm i.e. in austenite state. However, because the peri-articular soft tissue does not allow 5 mm of lengthening, the Nitinol device will be in a state of internal strain so a distraction force is generated. Because of the supra-elastic property of Nitinol, the distraction force is constant even when the peri-articular soft tissue lengthens by its viscoelastic property. The distraction force will decrease only when the soft tissue has been lengthened 5 mm. Such lengthening can only occur when the distraction force is excessively high and all the tissue including skin, subcutaneous tissue, ligaments, capsules are all partially torn.

During placement of the device, if it is done under an open technique, the collateral ligaments can be readily identified and the device can be inserted accurately. Even if the device is inserted percutaneously, it can be done under x-ray control. By using radiotransparent guide made up of the concentric circles, one can choose the size of the circle which matches the arc of the middle phalanx. The center of this circle corresponds to the axis of rotation of proximal interphalangeal joint. The device can be inserted into this point.

Figure 4:
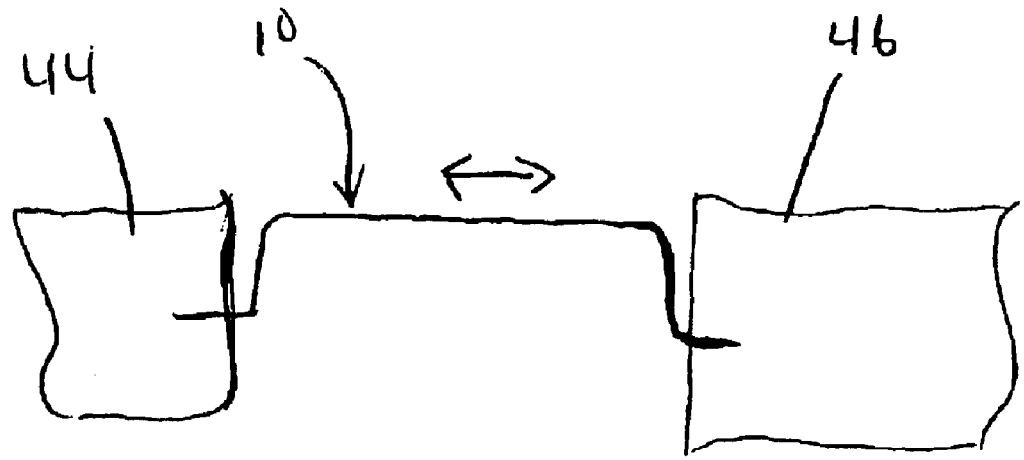
FIG. 4 shows a side view of the device inserted into a joint.

As shown in FIG. 4, the ends of device 10 can be inserted into two different bone sections 44 and 46 through a drill hole. The device is inserted into the bone in the martensite state, which is soft and easy to handle. This process is expected to be technically easy. Once it is in the bone, it is heated by a person's body into its strong austenite state, wherein the hooks 22 and 32 at the ends, will lock device 10 firmly in the bone.

As the device is designed for resisting axial loading, it would be inserted into both sides of the joint to give an even distraction force.

The strength of a material to resist axial compression or tension is proportional to the square of the cross-sectional area. The diameter of the device can be varied to give different quantities of distraction force.

Clinical Implications

The device is suitable to be used as distraction device in interphalangeal joint fractures and dislocation of the hand. The more common joint involvement is the proximal interphalangeal joint.

The distraction force of the device can be adjusted to its most optimal amount by varying the diameter of the Nitinol wire. The change in axial compression or distraction strength is proportional to the square of its diameter.

The hooks create a self-locking mechanism once the device is heated and changed to its austenite state. The device will not slip out once it is inserted onto the bone. The distraction force will be constant once it has been inserted. To remove the device is easy. Just by cooling it, it will change to martensite state, shrink back in length to thus pull out of the bones in the joint so that it can be pulled out easily.

Because this device is formed as a small metallic wire, it will not hinder movement of other normal digits, unlike other external distraction devices. It can be completely buried under skin so there will not be pin tract problems, like infection of skin impingement. The wound can be sutured primarily. If the surgeon wants to be minimally invasive, it can be inserted percutaneously.

The device is also applicable to other parts of musculoskeletal system where distraction force is required. Distraction osteosynthesis is currently done by an external fixator with threaded rods and the lengthening is done intermittently. The supra-elasticity of Nitinol can give more constant distraction force. Ligamentosis is adopted to treat fractures in various areas e.g. fracture distal radius, distal tibia, basal fracture of metacarpal of thumb. The device has potential use in these areas.

Accordingly, while at least one embodiment of the present invention has been shown and described, it is to be understood that many changes and modifications may be made thereunto without departing from the spirit and scope of the invention as defined in the appended claims.

What is claimed is:

1. A process for treating a interphalangeal joint fracture comprising:
    providing at least one nitinol wire having an S-shaped section and two ends wherein each of said two ends forms a hook for hooking into a bone section of a fractured bone;
    cooling said nitinol wire below a transfer temperature such that said nitinol wire forms in a martensite state;
    inserting said nitinol wire into a interphalangeal bone underneath a patients skin;
    allowing said nitinol wire to heat up above said transfer temperature inside a patient's body; and
    transforming said nitinol wire to from a martensite state to an austenite state wherein when said nitinol wire elongates in a longitudinal direction to generate a distraction force.

2. The process as in claim 1, wherein said transfer temperature is between 25° C. and 35° C.

3. The process as in claim 1, wherein during said transformation step, said ends insert into said interphalangeal bone and hook into said bone.

4. The process as in claim 1, wherein said step of inserting said nitinol wire includes inserting said nitinol wire percutaneously under x-ray control.

* * * * *